US008936151B2

(12) United States Patent
Abene et al.

(10) Patent No.: US 8,936,151 B2
(45) Date of Patent: Jan. 20, 2015

(54) DENTAL INSTRUMENT SECURING SYSTEM

(76) Inventors: Michael Abene, Taunton, MA (US); Benjamin G. Arany, Jr., Clearwater, FL (US); Michael H. Averell, Richmond, ME (US)

( * ) Notice: Subject to any disclaimer, the term of this patent is extended or adjusted under 35 U.S.C. 154(b) by 0 days.

(21) Appl. No.: 13/088,349

(22) Filed: Apr. 16, 2011

(65) Prior Publication Data

US 2012/0094249 A1 Apr. 19, 2012

Related U.S. Application Data

(60) Provisional application No. 61/325,295, filed on Apr. 17, 2010.

(51) Int. Cl.
*A61C 19/02* (2006.01)
*B65D 85/20* (2006.01)

(52) U.S. Cl.
USPC ............................ 206/369; 206/63.5; 206/565

(58) Field of Classification Search
USPC ........ 206/63.5, 570, 369, 488, 560, 565, 368, 206/486; 433/77; 211/69, 66, 65, 69.1, 211/60.1; 248/27.3, 27.1
See application file for complete search history.

(56) References Cited

U.S. PATENT DOCUMENTS

| | | | | | |
|---|---|---|---|---|---|
| 3,248,167 | A | * | 4/1966 | Friedman | 433/25 |
| 3,938,253 | A | * | 2/1976 | Barnard et al. | 433/75 |
| 4,253,830 | A | * | 3/1981 | Kazen et al. | 433/77 |
| 4,341,312 | A | * | 7/1982 | Scholer | 211/70.6 |
| 5,004,103 | A | * | 4/1991 | Connors et al. | 206/372 |
| 5,344,012 | A | * | 9/1994 | Matthews | 206/372 |
| 5,368,161 | A | * | 11/1994 | Plais | 206/369 |
| 5,464,348 | A | * | 11/1995 | Fischer et al. | 433/26 |
| 5,518,115 | A | * | 5/1996 | Latulippe | 206/370 |
| 5,525,314 | A | * | 6/1996 | Hurson | 422/300 |
| 5,603,899 | A | * | 2/1997 | Franciskovich et al. | 422/527 |
| 5,913,422 | A | | 6/1999 | Cote et al. | |
| 6,206,192 | B1 | * | 3/2001 | Winstead et al. | 206/572 |
| 6,585,942 | B1 | | 7/2003 | Bussell et al. | |
| 6,719,560 | B2 | * | 4/2004 | Capt | 433/77 |
| 7,066,329 | B2 | | 6/2006 | Riley | |
| 7,331,450 | B2 | | 2/2008 | Discko | |
| 2005/0019237 | A1 | | 1/2005 | Riley | |

OTHER PUBLICATIONS

Cynthia Bissel, RN, "Aaron's Tracheostomy Page" www.tracheostomy.com.

* cited by examiner

*Primary Examiner* — Steven A. Reynolds
(74) *Attorney, Agent, or Firm* — Banner & Witcoff, Ltd.

(57) ABSTRACT

A tray assembly for use with dental instruments is disclosed herein having a tray, a plate having a top plane and a bottom plane and apertures, the apertures being horizontally configured to receive a plurality of receiver assemblies supported on a top plane via a receiver assembly support, a plurality of semi-cylindrical Radel® instrument supports, a biasing instrument stationer whereby the instrument is friction held in stasis between the stationer and the instrument support, and a plurality of instrument stationers. The plate includes a plurality of aperture(s), at least one receiver assembly for receiving at least one medical/dental instrument inserted between the instrument support and the biasing instrument stationer, suspended within the tray. A kit is also disclosed for the present invention.

18 Claims, 4 Drawing Sheets

DENTAL INSTRUMENT SECURING SYSTEM

This application is a non-provisional of, and claims the benefit of the filing date of U.S. Provisional application No. 61/325,295 filed on Apr. 17, 2010. The Present invention relates generally to the field of dental instrument storage.

BACKGROUND OF THE INVENTION

Trays are often used to store and transport medical tools such as dental instruments for safekeeping and cleaning processes. It is crucial that the tools stored in these trays are properly sterilized and housed to protect users from accidental injury and patients from infection. Several devices are known that provide a way for a dental instrument to be secured and/or sanitized within a tray. Among these are restraints comprised of elastomeric materials such as silicon. One such restraint comprises a ring the instrument may be inserted into. Another utilizes a series of tabs to surround the instrument. Advantageously, all of these devices, especially when using a series of tabs, function to hold an instrument vertically in place in a tray, as opposed to simply resting the tool horizontally on the bottom of the tray.

BRIEF SUMMARY OF THE INVENTION

The known instrument securing devices do not adequately secure an instrument because they merely employ passive restraints comprised of elastomeric materials. As the elastomeric material degrades and becomes more porous over time, complete sterilization is compromised due to residual pathogens remaining in the material. Further, passive restraint systems lose their elasticity and the instrument becomes less secure as it is held in the tray.

At the heart of the present invention is the discovery that a multi-part, rigid, active restraint system can properly secure an instrument within the tray to prevent the user from accidental injury during use, storage, and transport of the instrument(s). In accordance with the invention, then, a dental instrument securing system configured to secure one or more dental instruments using the system described above is provided. Such a system includes at least one instrument support and a biasing means comprised of a non-elastomeric material. Such a system works to more effectively secure a dental instrument within a tray for sterilization, storage, and transport for easy removal.

Various other objects, features, and advantages of the invention will become readily apparent by reading the following description in conjunction with the drawings, which are shown by way of example only. The preferred embodiments of the present invention will hereinafter be described in conjunction with the appended drawings, wherein like designations denote like elements.

DETAILED DESCRIPTION

Figure 1:
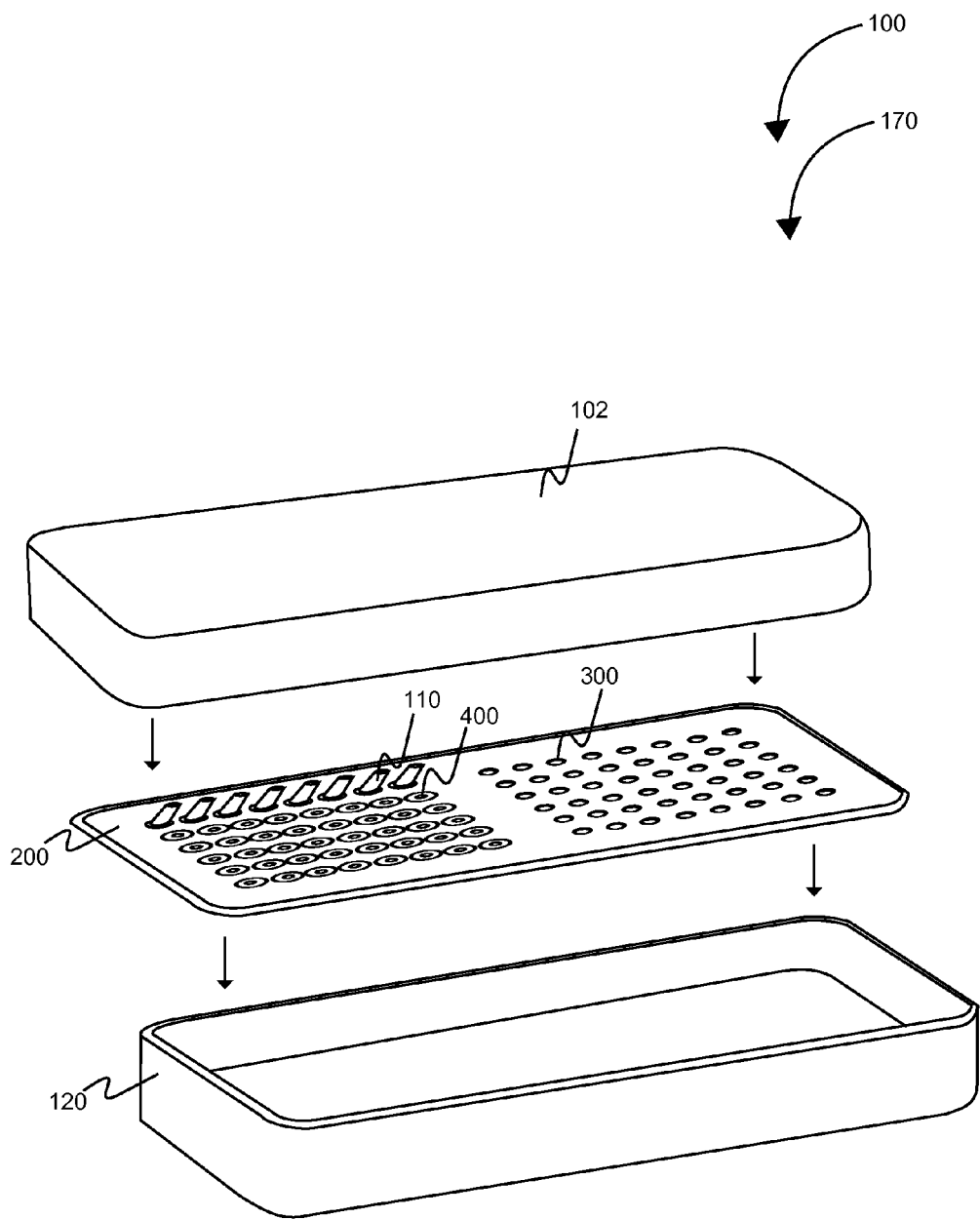
FIG. 1 shows a perspective view illustrating a dental instrument securing system embodying the principles of the present invention.

Referring now to the drawings in detail, this invention will be described by way of example and with reference to preferred embodiments thereof, however, it is to be understood that modifications and improvements may be made without departing from the scope or spirit of the invention. It should be noted that various changes and modifications to the presently preferred embodiments described herein will be apparent to those skilled in the art. Such changes and modifications may be made without diminishing its attendant advantages. It is, therefore, intended that such changes and modifications be included within the present invention.

Referring now to FIG. 1, showing a perspective view illustrating dental instrument securing system 100 embodying the principles of the present invention. Dental instrument securing system 100 is shown comprising at least one tray 120; at least one plate 200 having a plurality of receiver assembly support 300; a plurality of receiver assembly 400 for vertically securing dental instruments 110; and, optionally, at least one lid 102.

Tray 120 within the present invention may house and support the various components of dental instrument securing system 100 and may be of any size to work with standard laboratory equipment. Further, tray 120 may be comprised of any sturdy material, including materials capable of withstanding harsh conditions (such as those in an autoclave or dishwasher). Such materials may include polymers and plastics, metals such as aluminum, stainless steel, and the like, metal alloys, or any other material suitable for such purpose. It should be appreciated that other suitable materials may be used if desired and still be considered to be within the scope of the disclosed invention.

The dimensions of plate 200 may be complementary to the dimensions of tray 120 such that plate 200 may be removably received by tray 120. Further, plate 200 may be comprised of any material capable of withstanding harsh conditions (such as those in an autoclave or dishwasher). Such materials may include polymers and plastics, metals such as aluminum, stainless steel, and the like, metal alloys, or any other material suitable for such purpose. It should be appreciated that other suitable materials may be used if desired and still be considered to be within the scope of the disclosed invention.

Also shown within FIG. 1 is kit 170 including tray 120, optionally lid 102, at least one plate 200; a plurality of receiver assembly(ies) 400 (as also shown and discussed in FIGS. 2, 3, and 4), a plurality of receiver assembly support(s) 300 (as also shown and discussed in FIGS. 2, 3, and 4) and may include detailed instructions for proper use. Upon reading this specification, it should be noted that, under appropriate circumstances, when considering such issues as user, design, and marketing preferences, cost considerations, structural requirements, available materials, technological advances, etc., other kit contents such as, for example, including more or less components, customized parts, different color combinations, parts may be sold separately, etc., may present a suitable alternative.

Lid 102 within the present invention may cover tray 120 and/or the various components of dental instrument securing system 100 and may be of any size to work with standard laboratory equipment. Further, lid 102 may be comprised of any material capable of withstanding harsh conditions (such as those in an autoclave or dishwasher). Such materials may include polymers and plastics, metals such as aluminum, stainless steel, and the like, metal alloys, or any other material suitable for such purpose. It should be appreciated that other suitable materials may be used if desired and still be considered to be within the scope of the disclosed invention.

Figure 2:
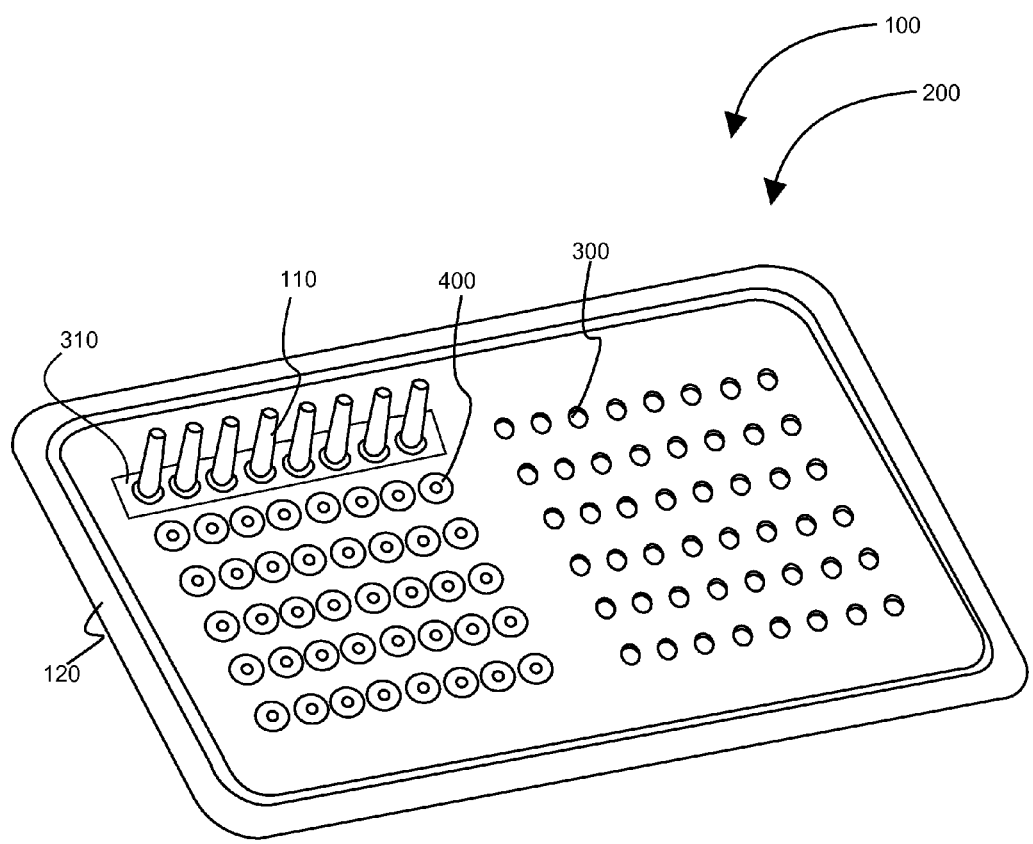
FIG. 2 shows a perspective top view of a plate and a receiver assembly embodying the principles of the present invention.

Referring now to FIG. 2, showing a perspective top view of plate 200 and similarly illustrating a perspective top view of receiver assembly 400 according to an embodiment of the present invention. As mentioned in FIG. 1, plate 200 may comprise a plurality of receiver assembly support 300 and may be removably received by tray 120. By way of example only, plate 200 is shown comprising forty eight (48) receiver assembly(s) 400 within forty eight (48) receiver assembly support(s) 300. Receiver assembly(s) 400 and receiver assembly support(s) 300 as depicted in FIG. 2 are arranged in parallel rows of 8. FIG. 2 also depicts, by way of example, eight (8) dental instrument 110. It should be understood this arrangement is exemplary; other configurations and/or arrangements of receiver assembly(s) 400 and/or receiver assembly support(s) 300 are contemplated without departing from the scope and spirit of the present invention.

FIG. 2 also shows plate 200 comprising forty eight (48) receiver assembly support(s) 300 without receiver assembly(s) 400 (as illustrated on the right side of plate 200). It should be understood that this configuration is optional; it is contemplated within the scope of the present invention that receiver assembly support 300 may be independent of other receiver support assembly(s) 300. For example, it is possible to stamp a series of receiver support assemblies 300 independent of each other, or, in the alternative, it is possible to insert them in group(s) 310 as shown. It should be understood that group 310 of receiver assembly 400 and receiver assembly support 300 may be any user-determined number sufficient to fit within plate 200. In this manner, the user may select any number of receiver assembly support 300 and/or receiver assembly 400 to fit his or her unique needs.

Figure 3:
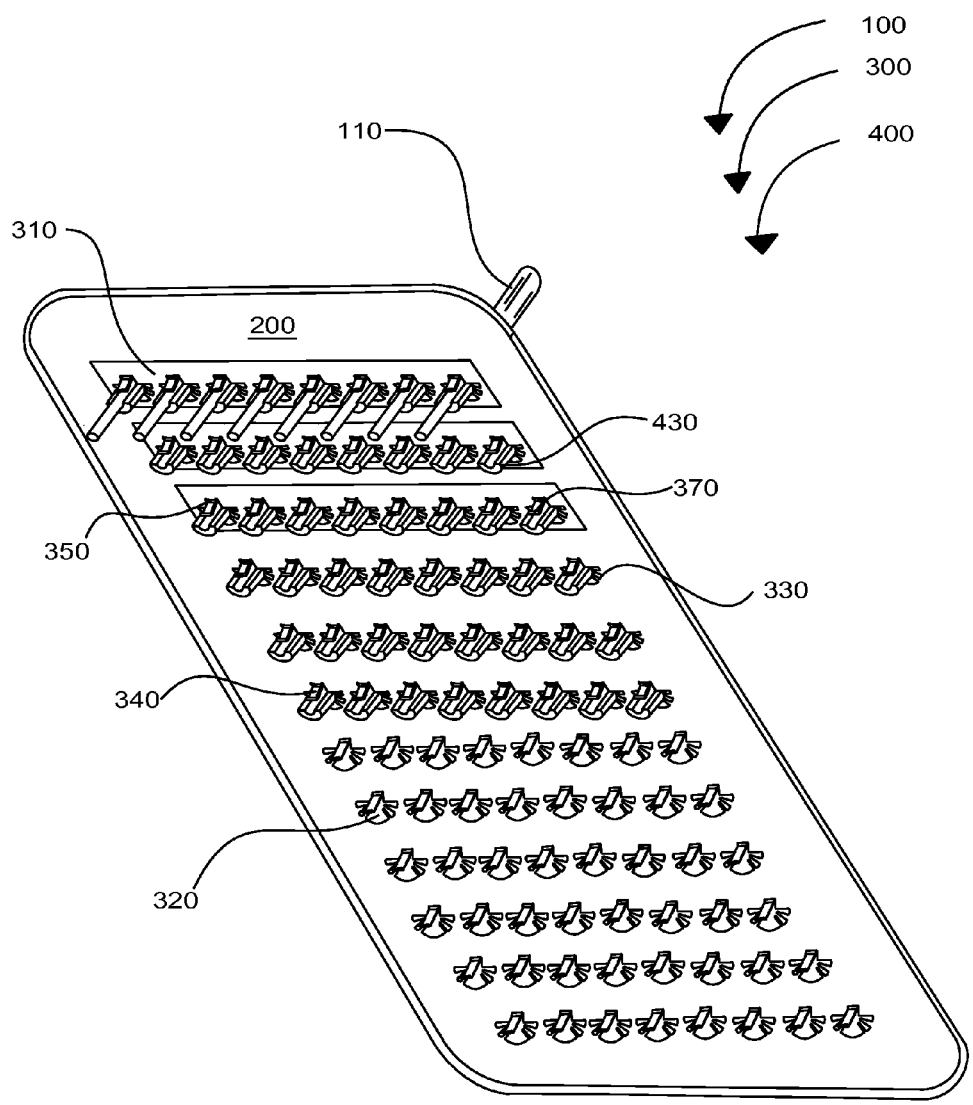
FIG. 3 shows a perspective underside view of a plate, a receiver assembly, and a receiver assembly support according to an embodiment of the present invention.

Referring now to FIG. 3, showing a perspective underside view of plate 200 and similarly illustrating a perspective underside view of receiver assembly support 300 and receiver assembly 400 according to an embodiment of the present invention. As illustrated in FIG. 3, and by way of example only, plate 200 is shown comprising three (3) group 310 of eight (8) receiver assembly support 300 containing eight (8) receiver assembly 400 and eight (8) dental instrument 110 per group 310; twenty four (24) individually stamped receiver assembly support 300 containing twenty four (24) receiver assembly 400; and forty eight (48) receiver assembly support 300 without receiver assembly 400. It should be understood that the parallel configuration as depicted in FIG. 3 is optional. Receiver assembly support(s) 300 and/or receiver assembly 400 may be in spaced parallel relation to one another within plate 200 as depicted in FIG. 3, however in other embodiments (not shown) the space-relation may be diagonal, perpendicular, or any other suitable polylinear configuration.

Receiver assembly support 300 may be preferably press fit into plate 200. Receiver assembly 400 may be similarly press fit together within receiver assembly support 300. In this manner, these three components of dental instrument securing system 100 operate in concert to provide active restraint of dental instrument 110. In alternative embodiments, receiver assembly support 300 and/or receiver assembly 400 may be stamped into or cut out of plate 200.

As illustrated in FIG. 3 and further discussed in FIG. 4, receiver assembly 400 may bisect plate 200 such that instrument support 430 is substantially located on the lower portion of plate 200 as shown. In this manner, grommet 450 (shown in FIG. 2) may be substantially above receiver assembly support 300 while instrument support 430 may be substantially below receiver assembly support 300 as shown. Receiver assembly support 300 substantially secures receiver assembly 400 by creating a sealed friction fit with grommet 450 and aperture 320 on top portion of plate 200, as shown in FIGS. 2, 3, and 4.

As illustrated in FIG. 3, and mentioned above, receiver assembly support 300 may comprise aperture 320. In a preferred embodiment, the dimensions of receiver assembly support 300 are complementary to the dimensions of receiver assembly 400 such that aperture 320 is capable of removably receiving at least one receiver assembly 400 as shown. In this manner, receiver assembly 400 is held in stasis with receiver assembly support 300 within plate 200. Aperture 320 may be positioned substantially beneath grommet 450 (discussed in FIG. 4).

Receiver assembly support 300 may further comprise a plurality of anchoring means 330 to suitably secure receiver assembly 400. When receiver assembly 400 is inserted through aperture 320 and bisects plate 200, at least one anchoring means 330 actively restrains receiver assembly 400 by remaining in constant contact with instrument support 430 as shown. In this manner, receiver assembly 400 is held in stasis with receiver assembly support 300 within plate 200. Aperture 320 may further comprise instrument stationer 340, and joint 350. Instrument stationer 340 may be located on the underside of plate 200 substantially beneath grommet 450 (discussed in FIG. 4) on the lower portion of plate 200.

Instrument stationer 340 within the present embodiment comprises joint 350 and lip 370. As further discussed in FIG. 4, instrument stationer 340 is designed to provide increased securing of dental instrument 110 and to decrease the opportunity for accidental abrasion of the lower portion of dental instrument 110. Lip 370 may be located on the distal end of instrument stationer 340. Lip 370 may further be substantially facing upward from instrument support 430 as shown. In this manner, lip 370 permits instrument stationer 340 to securely hold dental instrument 110 in place against instrument support 430 while at the same time preventing damage to the instrument from chafing or scratching by instrument stationer 340.

Joint 350 provides flexibility to instrument stationer 340 to permit it to function as a biasing means to secure and hold dental instrument 110. Joint 350 may be substantially within the bottom plane of plate 200 within receiver assembly support 300, as shown. Instrument stationer 340 works in concert with joint 350 and lip 370 to hold the lower portion of dental instrument 110 in stasis with instrument support 430, vertically as shown.

Figure 4A:
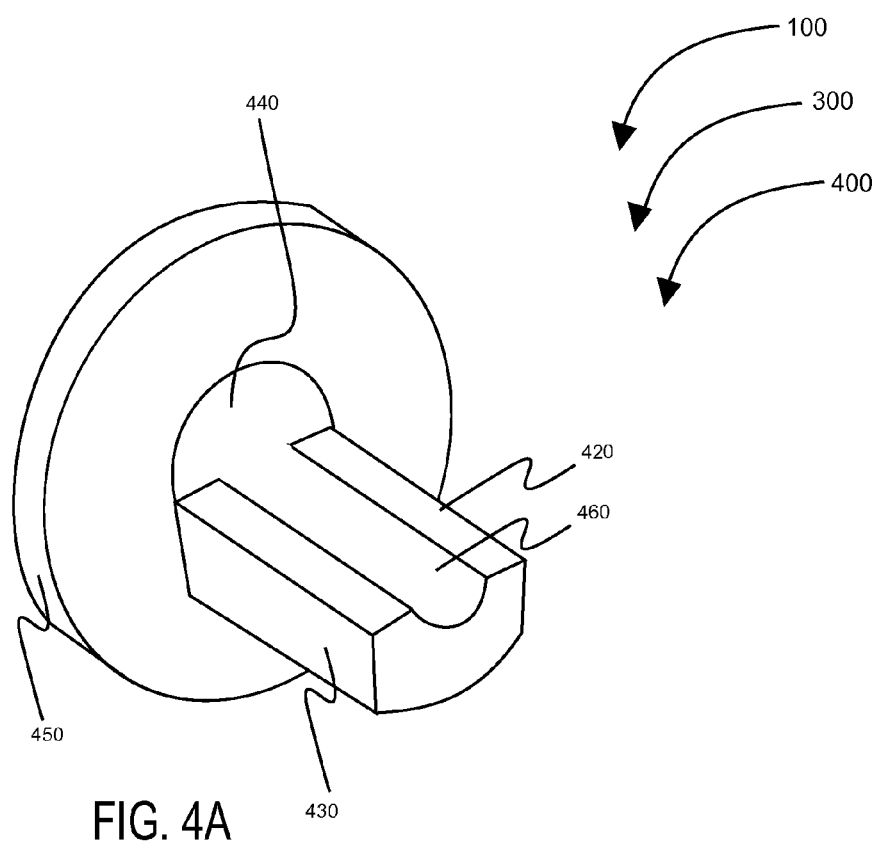
FIG. 4, consisting of FIGS. 4A and 4B, is a perspective view illustrating a receiver assembly and receiver assembly support according to an embodiment of the present invention.
Figure 4B:
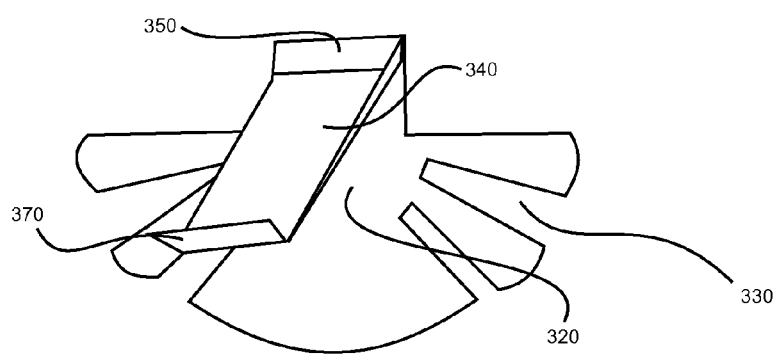

Referring now to FIG. 4, consisting of FIGS. 4A and 4B, and illustrating receiver assembly 400 and receiver assembly support 300 according to a preferred embodiment of the present invention of FIGS. 1-4. Receiver assembly 400 may comprise instrument support 430, second aperture 440, and grommet 450. Receiver assembly 400 may be comprised of any sturdy, non elastomeric material capable of withstanding harsh conditions such as those found in an autoclave or dishwasher; however the preferred material within this particular embodiment is Radel®. It should be understood that other non-elastomeric materials suitable for the purpose of securing and protecting dental instruments 110 may be used if desired, such as polymers and plastics, metal and metal alloys, and the like.

As mentioned in FIG. 3, instrument support 430 may be molded with grommet 450 and function in concert with instrument stationer 370 to secure, protect, and hold in stasis dental instrument 110. Grommet 450 may function as the upper portion of receiver assembly 400. Further, grommet 450 may positioned substantially over aperture 320 (shown FIG. 2 and discussed in FIG. 3) and serves additionally to provide a sealing means between aperture 320 and lower portion 420 of receiver assembly 400 within plate 200. In this manner, instrument support 430 may inserted into aperture 320 and occupy the space underneath plate 200 while grommet 450 may occupy the space over aperture 320 and on the upper surface of plate 200.

Receiver assembly 400 may further comprise second aperture 440 for removably receiving and securing dental instrument 110. Further, instrument support may further comprise rest 460. When he or she wishes to store and/or transport medical equipment such as dental instruments, the user may insert dental instrument 110 through aperture 320 into second aperture 440 such that the lower portion of dental instrument 110 is positioned substantially against rest 460 (as depicted in FIGS. 1-3).

Grommet 450 preferably comprises a non-elastomeric material such as Radel® to provide a sealed-fit of receiver assembly 400 within plate 200. This substantially reduces the chance of contamination, degradation, and erosion of secure instrument retention. In this way, the present invention promotes safe, effective, reliable and efficient instrument retention. Further, use of a non-elastomeric material such as Radel® increases longevity of dental instrument securing system 100 and its components with repeated use over time. It should be understood that other non-elastomeric materials may be utilized without departing from the scope and spirit of the present invention.

Instrument support 430 may be substantially semi-cylindrical in shape as illustrated in FIG. 4. However, it is contemplated within the scope of the present invention that other shapes may be utilized to accomplish the task of supporting a laboratory instrument. In this manner, anchoring means 320 may be in contact with the outer portion of instrument support 430 while dental instrument 110 may be in contract with the inner portion of instrument support 430 as shown. As with all other components of receiver assembly 400, rest 460 may be comprised of any non-elastomeric material, with Radel® being preferred. Further, rest 460 may be cylindrical as shown. In alternative embodiments, rest 460 may be cuboid, prismatoid, or any other polyangular shape sufficient to retain an instrument. In certain embodiments, receiver assembly 400 may be color coded according to the user specifications for example, for use in tool identification, organization, and other such uses. It should be understood that receiver assembly support may accommodate any tool such as standard medical or laboratory equipment and is not limited to dental tools.

As shown in FIGS. 2, 3, and 4, dental instrument(s) 110 may be frictionally inserted into second aperture 440 as also shown in FIGS. 2 and 3 such that the lower portion of dental instrument 110 (such as a needle, probe, or a blade) is substantially located in or about the underside of plate 200, while the upper portion of dental instrument 110 (such as a handle or grip) is substantially located above the top portion of plate 200. Dental instrument 110 is preferably inserted into receiver assembly 400 in a substantially vertical orientation and is in constant stationary contact with grommet 450 (as depicted in FIG. 1), instrument stationer 340 and rest 460. Instrument stationer 340 is adjacent to and works in concert with aperture 320 to actively secure dental instrument 110 within receiver assembly 400 by compressing the lower portion of dental instrument 110 against instrument support 430. In this manner, dental instrument 110 is held in stasis between support 430 and stationer 340 via friction fit. In this way the present invention provides the necessary support means and at the same time secures dental instrument 110 within dental instrument securing system 100.

From the foregoing description, it should be appreciated that a dental instrument securing system 100 preferred embodiment is provided and present significant benefits that would be apparent to one skilled in the art. Furthermore, it should be appreciated that a vast number of variations in the embodiments exist. Lastly, it should be appreciated that these embodiments are preferred exemplary embodiments only, and are not intended to limit the scope, applicability, or configuration of the invention in any way. Rather, the foregoing detailed description provides those skilled in the art with a convenient framework for implementing a preferred exemplary embodiment of the invention. It being understood that various changes may be made in the function and arrangement of elements described in the exemplary preferred embodiment without departing from the spirit and scope of the invention as set forth.

What is claimed is:

1. A dental instrument securing system for use in an autoclave comprising:
    at least one plate comprising at least one aperture having at least one stationing means and at least one tab wherein said at least one stationing means and said at least one tab work in concert to actively restrain an instrument;
    at least one tray;
    a plurality of instrument holders having a support means having a cavity for securely holding said at least one dental instrument and at least one grommet for suspending said instrument holder within said plate via said at least one aperture; wherein said instrument holder comprises a non-elastomeric polymer; and
    wherein said aperture supports at least one of said plurality of instrument holders.

2. The dental instrument securing system of claim 1 further comprising a lid.

3. The dental instrument securing system of claim 1 wherein said tray removably receives said at least one said plate.

4. The dental instrument securing system of claim 1 wherein said support means bisects said plate via said at least one aperture.

5. The dental instrument securing system of claim 1 wherein said instrument holders are inserted through said at least one aperture.

6. The dental instrument securing system of claim 1 wherein said at least one tab is in contact with said support means.

7. The dental instrument securing system of claim 1 wherein said support means is substantially beneath said at least one aperture.

8. The dental instrument securing system of claim 1 wherein said at least one grommet is substantially above said aperture.

9. The dental instrument securing system of claim 1 wherein said at least one stationing means further comprises a joint.

10. The dental instrument securing system of claim 9 wherein said joint is on the distal portion of said at least one stationing means.

11. The dental instrument securing system of claim 1 wherein said at least one stationing means secures an instrument against said instrument holder.

12. The dental instrument securing system of claim 10 wherein said instrument rests vertically against said support means.

13. The dental instrument securing system of claim 10 wherein a handle of said instrument is substantially above said at least one aperture.

14. The dental instrument securing system of claim 10 wherein a handle of said instrument is substantially over said at least one grommet.

15. The dental instrument securing system of claim 1 wherein a lower portion of said instrument is in contact with said at least one stationing means.

16. The dental instrument securing system of claim 1 wherein said lower portion of said instrument is in contact with said instrument holder.

17. The dental instrument securing system of claim 1 further comprising a kit wherein the kit includes said at least one tray, a lid, said at least one plate, wherein said at least one plate further comprises a user determined number of apertures, a user determined number of instrument holders, and detailed instructions for use.

18. An instrument securing system for use in an autoclave comprising:

an instrument receiver, having at least one instrument support, at least one aperture, and at least one grommet, said at least one instrument support partially enclosing at least one instrument;

a support means for said instrument receiver, having at least one tab, at least one opening, and at least one stationer, said at least one tab remaining in contact with said instrument support and said at least one stationer in contact with at least one instrument;

wherein said at least one stationer and said at least one tab work in concert to actively restrain said at least one instrument;

wherein said at least one instrument is inserted through said at least one opening into said at least one aperture; and wherein said instrument support comprises an elastomeric polymer;

and wherein said at least one instrument is actively restrained against said at least one instrument support by said at least one stationer.

* * * * *